(12) United States Patent
Takemura et al.

(10) Patent No.: US 9,442,054 B2
(45) Date of Patent: Sep. 13, 2016

(54) HARDNESS TESTER HAVING OFFSET CORRECTION FEATURE

(71) Applicant: MITUTOYO CORPORATION, Kanagawa (JP)

(72) Inventors: Fumihiro Takemura, Brussels (BE); Fumihiko Koshimizu, Zama (JP)

(73) Assignee: MITUTOYO CORPORATION, Kanagawa (JP)

( * ) Notice: Subject to any disclaimer, the term of this patent is extended or adjusted under 35 U.S.C. 154(b) by 303 days.

(21) Appl. No.: 13/832,631

(22) Filed: Mar. 15, 2013

(65) Prior Publication Data

US 2013/0258094 A1    Oct. 3, 2013

(30) Foreign Application Priority Data

Mar. 27, 2012   (JP) ................. 2012-070581

(51) Int. Cl.
  *G01N 3/42*    (2006.01)
  *G01N 3/06*    (2006.01)

(52) U.S. Cl.
  CPC .......... *G01N 3/068* (2013.01); *G01N 3/42* (2013.01); *G01N 2203/0003* (2013.01); *G01N 2203/008* (2013.01); *G01N 2203/0019* (2013.01)

(58) Field of Classification Search
  CPC .................................................. G01N 3/068
  See application file for complete search history.

(56) References Cited

U.S. PATENT DOCUMENTS

| | | | | |
|---|---|---|---|---|
| 4,147,052 A | * | 4/1979 | Tsujiuchi | G01N 3/42 356/626 |
| 4,255,966 A | * | 3/1981 | Batie | G01B 11/024 73/81 |
| 4,463,600 A | * | 8/1984 | Hobbs | G01B 11/285 356/626 |
| 4,653,106 A | * | 3/1987 | Yamatsuta | G01B 11/024 348/86 |
| 5,146,779 A | * | 9/1992 | Sugimoto | G01N 3/40 356/626 |

(Continued)

FOREIGN PATENT DOCUMENTS

| | | |
|---|---|---|
| JP | 63-057562 | 4/1988 |
| JP | H05-133865 | 5/1993 |

(Continued)

OTHER PUBLICATIONS

U.S. Appl. No. 13/828,164 to Fumihiro Takemura et al., filed Mar. 14, 2013.

(Continued)

*Primary Examiner* — Jay Patel
*Assistant Examiner* — Irfan Habib
(74) *Attorney, Agent, or Firm* — Greenblum & Bernstein, P.L.C.

(57) ABSTRACT

A hardness tester enabling a user to form an indentation in a desired test position, capable of performing an accurate hardness test even when center positions of an indenter and a field lens are offset. The hardness tester includes an XY stage displacing a sample stage in a horizontal direction; a CCD camera capturing images of a sample surface via a field lens; a monitor displaying the images; a turret capable of selectively positioning the indenter or the field lens in a predetermined position opposite the sample; a memory storing an amount of horizontal direction offset between the center positions of the indenter and the field lens when positioned in the predetermined position; and a CPU displaying, based on the amount of offset stored in the memory, a mark indicating the center position of the indenter on the monitor when the field lens is positioned in the predetermined position.

12 Claims, 17 Drawing Sheets

(56) References Cited

U.S. PATENT DOCUMENTS

| | | | | |
|---|---|---|---|---|
| 5,355,721 | A * | 10/1994 | Las Navas Garcia | G01B 7/28 73/82 |
| 5,804,707 | A * | 9/1998 | Scarton | G01N 3/48 73/82 |
| 6,247,356 | B1 * | 6/2001 | Merck, Jr. | G01N 3/42 73/82 |
| 6,279,388 | B1 * | 8/2001 | Tsujii | G01N 3/42 73/82 |
| 6,301,956 | B1 * | 10/2001 | Fujita | G01N 3/42 73/78 |
| 6,336,359 | B1 * | 1/2002 | Kawazoe | G01N 3/40 73/81 |
| 6,457,349 | B1 * | 10/2002 | Miyahara | G01N 3/48 73/78 |
| 7,096,720 | B2 * | 8/2006 | Hayashi | G01N 3/42 702/33 |
| 7,121,136 | B2 * | 10/2006 | Tsujii | G01N 3/42 73/78 |
| 7,380,443 | B2 * | 6/2008 | Tsujii | G01N 3/42 73/81 |
| 7,412,870 | B2 * | 8/2008 | Brankov | G01N 3/303 73/12.11 |
| 7,516,644 | B2 * | 4/2009 | Wong | G01N 3/20 73/12.06 |
| 8,578,284 | B2 * | 11/2013 | Takemura | G01N 3/42 715/764 |
| 2003/0070475 | A1 * | 4/2003 | Nagashima | B82Y 35/00 73/81 |
| 2004/0096093 | A1 * | 5/2004 | Hauck | G01N 3/08 382/141 |
| 2004/0134263 | A1 * | 7/2004 | Tsujii | G01N 3/42 73/81 |
| 2005/0265593 | A1 * | 12/2005 | Hauck | G01N 3/08 382/141 |
| 2006/0288763 | A1 * | 12/2006 | Tsujii | G01N 3/42 73/81 |
| 2009/0226033 | A1 * | 9/2009 | Sefcik | G06K 9/3233 382/103 |
| 2012/0085154 | A1 | 4/2012 | Takemura et al. | |
| 2012/0087567 | A1 * | 4/2012 | Takemura | G01N 3/42 382/141 |
| 2012/0101743 | A1 * | 4/2012 | Sawa | G01N 3/42 702/41 |
| 2013/0047712 | A1 * | 2/2013 | Ariga | G01N 3/42 73/81 |
| 2013/0047713 | A1 | 2/2013 | Ariga | |
| 2013/0174653 | A1 * | 7/2013 | Sawa | G01N 3/42 73/82 |
| 2013/0319071 | A1 * | 12/2013 | Vodnick | G01B 21/047 73/1.08 |

FOREIGN PATENT DOCUMENTS

| | | |
|---|---|---|
| JP | 2004-286541 | 10/2004 |
| JP | 2011-220790 | 11/2011 |

OTHER PUBLICATIONS

Office Action issued in Japan Counterpart Patent Appl. No. 2012-070581, dated Dec. 22, 2015, along with an English translation thereof.

* cited by examiner

HARDNESS TESTER HAVING OFFSET CORRECTION FEATURE

CROSS-REFERENCE TO RELATED APPLICATIONS

The present application claims priority under 35 U.S.C. §119 of Japanese Application No. 2012-070581, filed on Mar. 27, 2012, the disclosure of which is expressly incorporated by reference herein in its entirety.

BACKGROUND OF THE INVENTION

1. Field of the Invention

The present invention relates to a hardness tester.

2. Description of Related Art

Conventionally, hardness testing methods of a pressing type are well known, such as the Vickers hardness test and the Knoop hardness test, in which an indenter having a planar polygonal shape is pressed against a surface of a sample, then a degree of hardness of the sample is measured from a length of a diagonal line in a resulting polygonal indentation in the sample surface. Such hardness testing methods are widely used in evaluating mechanical characteristics of metallic materials.

As is commonly known, the Vickers hardness test employs a quadrangular pyramid diamond indenter and indicates the degree of hardness by a relationship between an average value for the length of the two diagonal lines of the quadrangular pyramid indentation formed in the surface of the sample and a pressing load of the indenter on the sample. The Knoop hardness test employs a rhomboid pyramid diamond indenter and indicates the degree of hardness by a relationship between the length of the longer of the diagonal lines of the rhomboid pyramid indentation formed in the surface of the sample and the pressing load of the indenter on the sample.

Typically, when conducting a hardness test with the Vickers hardness test or the Knoop hardness test, the sample is observed with a field lens to set a test position. A turret is then rotated to replace the field lens with the indenter, and an indentation operation is performed. Then, the turret is switched back to the field lens once again to observe the indentation formed in the surface of the sample. At this point, in order to correctly form the indentation in the set test position, a center position of the indenter that will form the indentation and the center position of the field lens that will conduct the observation must be positioned correctly. In a conventional hardness tester, a centering mechanism is used to automatically adjust the field lens to match the center position of the indenter when the indenter is disposed, or positioned, in a predetermined position opposite the sample.

However, because the indenter is disposable (i.e., can be thrown away) the indenter must be changed when worn out. When the indenter is changed, the center position of the indenter and the center position of the field lens may become offset, thus creating a need to center the field lens. In order to center the field lens, indentation is performed with a reference indenter, then the turret is rotated to switch to the field lens to be centered. Next, while observing the indentation, the field lens is centered such that the center position of the indentation matches the center position on a screen. Finally, the turret switches to the indenter and performs another indentation, then switches to the centered field lens and confirms whether the center position of the indentation matches the center position on the screen.

Existing hardness testers are mounted with a large number of field lenses. Therefore, the above-described centering procedure must be performed for the number of field lenses installed. In addition, some of the existing hardness testers are mounted with two indenters, and thus a second indenter must be centered to match the center position of a first indenter serving as the reference. A user is burdened in performing the above-described sequence of centering work.

To address this, a hardness tester is disclosed that is capable of performing an accurate hardness test even when the center position of the indenter is offset from the center position of the field lens (see, e.g., Japanese Patent Laid-open Publication No. 2004-286541). Specifically, the invention described in Japanese Patent Laid-open Publication No. 2004-286541 calculates a coordinate differential between a center coordinate of a display screen (a field lens) and the center coordinate of an indentation displayed on the display screen. Then, the offset between the center position of the indenter and the center position of the field lens is corrected by displacing a sample stage in a horizontal direction such that the coordinate differential is approximately zero.

However, the invention described in Japanese Patent Laid-open Publication No. 2004-286541 is a correction process performed during hardness calculation after the indentation is formed and cannot correct the offset between the center position of the indenter and the center position of the field lens during formation of the indentation. Therefore, the user may be unable to form the indentation in a desired test position.

SUMMARY OF THE INVENTION

The present invention provides a hardness tester enabling a user to form an indentation in a desired test position and capable of performing an accurate hardness test even when a center position of an indenter and a center position of a field lens are offset.

One aspect of the present invention is a hardness tester measuring hardness of a sample placed on a sample stage by loading a predetermined test force on the sample with an indenter to form an indentation in a surface of the sample, then measuring dimensions of the indentation. The hardness tester includes a horizontal stage displacer, an image capturer, a display, a switcher, a memory, and a display controller. The horizontal stage displacer displaces the sample stage in a horizontal direction. The image capturer captures an image of the surface of the sample via a field lens. The display displays the image of the surface of the sample captured by the image capturer. The switcher is capable of selectively disposing one of the indenter and the field lens in a predetermined position opposite the sample. The memory stores an amount of offset in the horizontal direction between a center position of the indenter when disposed in the predetermined position and the center position of the field lens when disposed in the predetermined position. The display controller displays a mark indicating the center position of the indenter on the display based on the amount of offset stored in the memory when the field lens is disposed in the predetermined position by the switcher.

Another aspect of the present invention is the hardness tester in which the indenter includes a first indenter and a second indenter; in which the memory stores the amount of offset in the horizontal direction between the center position of the first indenter when disposed in the predetermined position and the center position of the second indenter when disposed in the predetermined position; and in which the display controller displays a mark indicating the center position of the first indenter and a mark indicating the center position of the second indenter on the display based on the amount of offset stored in the memory when the field lens is disposed in the predetermined position by the switcher.

Another aspect of the present invention is a hardness tester measuring hardness of a sample placed on a sample stage by loading a predetermined test force on the sample with an indenter to form an indentation in a surface of the sample, then measuring dimensions of the indentation. The hardness tester includes a horizontal stage displacer, an image capturer, a switcher, a memory, and a stage displacement controller. The horizontal stage displacer displaces the sample stage in a horizontal direction. The image capturer captures an image of the surface of the sample via a field lens. The switcher is capable of selectively disposing one of the indenter and the field lens in a predetermined position opposite the sample. The memory stores an amount of offset in the horizontal direction between a center position of the indenter when disposed in the predetermined position and a center position of the field lens when disposed in the predetermined position. The stage displacement controller displaces the horizontal stage displacer to a position corresponding to a center position of one of the indenter and the field lens when disposed in the predetermined position by the switcher, based on the amount of offset stored in the memory.

Another aspect of the present invention is the hardness tester in which the indenter includes a first indenter and a second indenter; in which the memory stores the amount of offset in the horizontal direction between the center position of the first indenter when disposed in the predetermined position and the center position of the second indenter when disposed in the predetermined position; and in which the stage displacement controller displaces the horizontal stage displacer to a position corresponding to the center position of one of the first indenter, the second indenter, and the field lens when disposed in the predetermined position by the switcher, based on the amount of offset stored in the memory.

Another aspect of the present invention is the hardness tester including a stage elevator raising and lowering the sample stage in a vertical direction. In the hardness tester according to this aspect, the memory stores an amount of offset in the vertical direction between a position of the sample stage when performing indentation with the indenter, the indenter being disposed in the predetermined position, and the position of the sample stage when the field lens is in focus, the field lens being disposed in the predetermined position. In addition, the stage displacement controller raises and lowers the stage elevator based on the amount of offset stored in the memory such that the sample stage is positioned in the position where the field lens is in focus, the field lens being disposed in the predetermined position by the switcher.

Another aspect of the present invention is the hardness tester in which the field lens includes a first field lens and a second field lens having a lower magnification than the first field lens. The hardness tester according to this aspect further includes an indentation determiner and an image compiler. The indentation determiner analyzes the image of the surface of the sample captured by the image capturer via the first field lens and determines whether the indentation formed by the indenter is present in the image. When the indentation determiner determines that the indentation is not present in the image, the image compiler captures a desired number of images with the image capturer while displacing the horizontal stage displacer in the horizontal direction in increments of a range enabling image capture each time an image is captured, displacement of the horizontal stage displacer being centered on a current position, then compiling the desired number of captured images into a single image.

According to the present invention, a user can form an indentation in a desired test position and an accurate hardness test can be performed even when center positions of an indenter and a field lens are offset.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

Hereafter, embodiments of the present invention are described with reference to the drawings. Moreover, in the following description, an X direction is a left-right direction, a Y direction is a front-back direction, and a Z direction is an up-down direction in FIGS. 1 and 13. In addition, an X-Y plane is a horizontal plane.

First Embodiment

Figure 1:
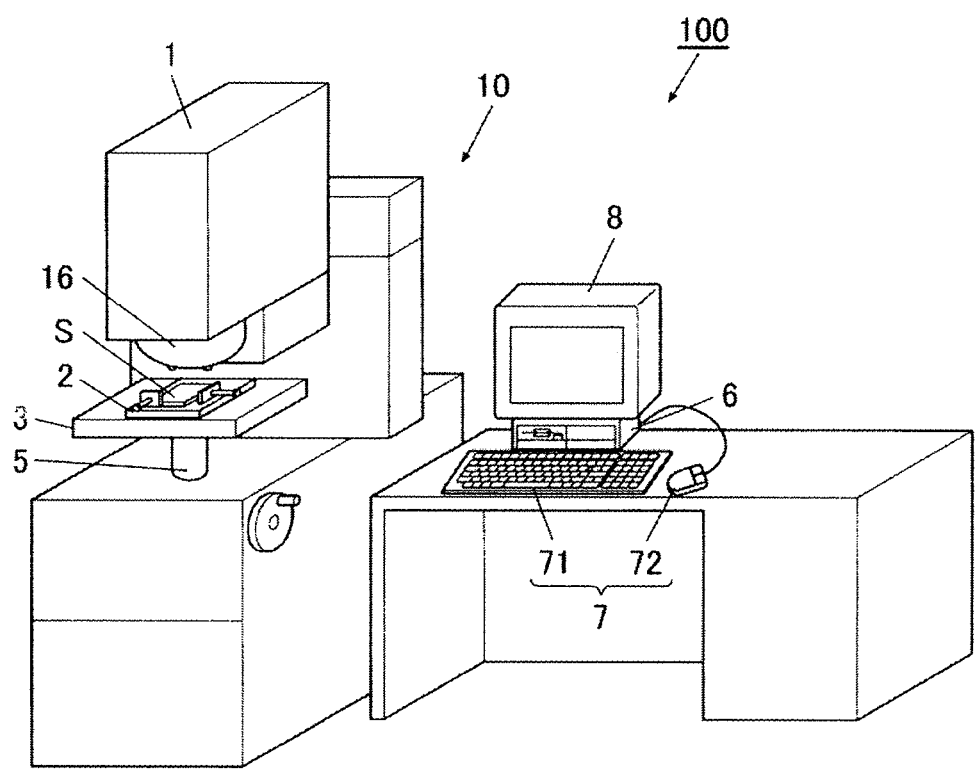
FIG. 1 is a perspective view illustrating an overall configuration of a hardness tester according to a first embodiment.
Figure 2:
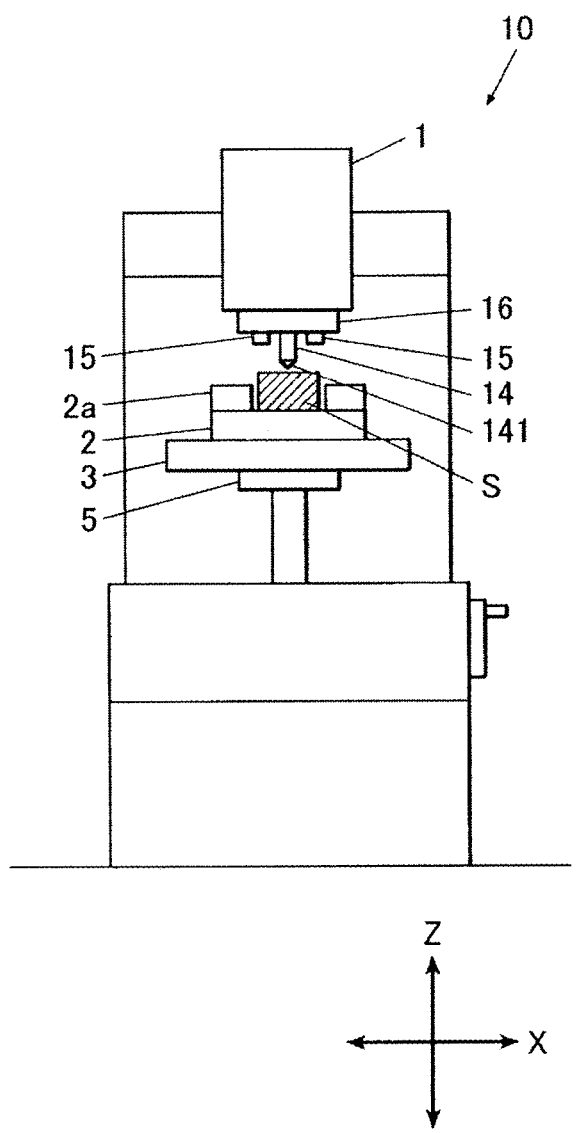
FIG. 2 is a schematic view illustrating a hardness tester main body of the hardness tester according to the first embodiment.

A hardness tester 100 according to a first embodiment is a hardness tester including a manual XY stage 3 and, as shown in FIGS. 1 and 2, includes a hardness tester main body 10, a controller 6, an operator 7, and a monitor 8.

The hardness tester main body 10 includes a hardness measurer 1 performing a measurement of hardness of a sample S; a sample stage 2 on which the sample S is placed; the XY stage 3 displacing the sample stage 2 in a horizontal direction; and an elevator mechanism 5 raising and lowering the sample stage 2 and the XY stage 3 in a vertical direction so as to focus on a surface of the sample S.

Figure 3:
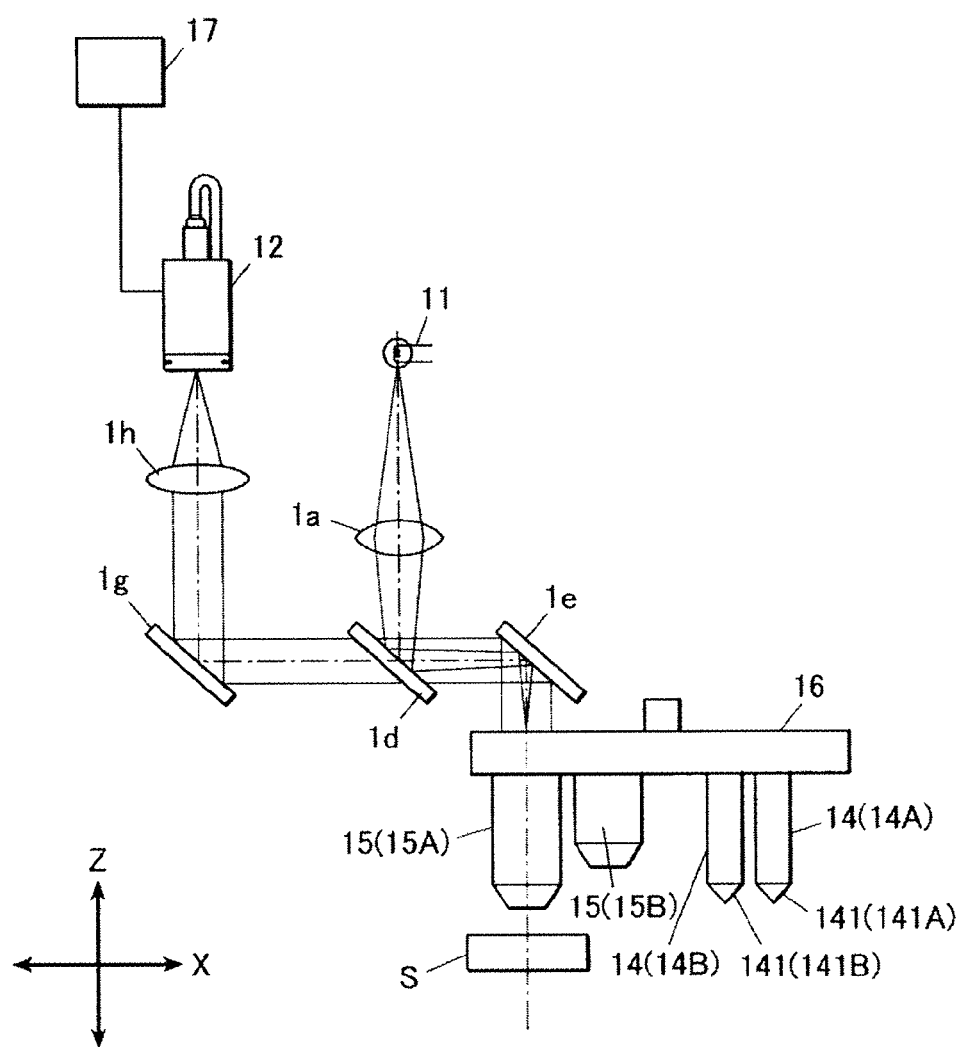
FIG. 3 is a schematic view illustrating a hardness measurer of the hardness tester according to the first embodiment.

As shown in FIG. 3, the hardness measurer 1 is configured with an illuminating device 11 illuminating the surface of the sample S; a CCD camera 12 capturing an image of the surface of the sample S; and a turret 16. The turret 16 includes two indenter axes 14 that include indenters 141 and two field lenses 15. The turret 16 is capable of switching between the indenter axes 14 and the field lenses 15 by rotating.

The illuminating device 11 shines a light to illuminate the surface of the sample S. The light shone by the illuminating device 11 reaches the surface of the sample S via a lens 1a, a half mirror 1d, a mirror 1e, and the field lenses 15.

Based on reflected light input from the surface of the sample S via the field lenses 15, the mirror 1e, the half mirror 1d, a mirror 1g, and a lens 1h, the CCD camera 12 obtains image data by capturing an image of the surface of the sample S as well as the indentation formed in the surface of the sample S by the indenter 141. The CCD camera 12 then outputs the image data to the controller 6 via a frame grabber 17, which is capable of simultaneously accumulating and storing a plurality of frames of image data. Thus, the CCD camera 12 is an image capturer.

A plurality of indenter axes 14 are held on a bottom surface of the turret 16 and are disposed above the sample S (i.e., in a predetermined position opposite the sample S) by rotation of the turret 16. Thereby, the indenter axes 14 are displaced toward the sample S placed on the sample stage 2 by a load mechanism (not shown in the drawings), which is driven in response to a control signal output by the controller 6. The indenter axes 14 thus press the indenters 141 against the surface of the sample S with a predetermined test force, the indenters 141 provided on a tip of the indenter axes 14. Specifically, the indenter axes 14 are configured to include a first indenter axis 14A and a second indenter axis 14B. The first indenter axis 14A includes a first indenter 141A used in a Vickers hardness test with a quadrangular pyramid diamond tip. The second indenter axis 14B includes a second indenter 141B used in a Knoop hardness test with a rhomboid pyramid diamond tip.

The field lenses 15 are collective lenses each configured with a different magnification. A plurality of the field lenses 15 are held on the bottom surface of the turret 16 and are disposed in the predetermined position opposite the sample S by rotating the turret 16. Thereby, the light shone by the illuminating device 11 uniformly illuminates the surface of the sample S. Specifically, the field lens 15 is configured to include a high-magnification field lens (first field lens) 15A and a low-magnification field lens (second field lens) 15B having a magnification lower than that of the high-magnification field lens 15A. The high-magnification field lens 15A is more preferably a lens having a magnification of twenty times or greater. When a lens having a magnification of twenty times or greater is used, a field depth is shallow and does not exceed an allowed range for height of the sample S during indentation. Thus, positioning accuracy for the height of the sample S can be improved. Meanwhile, the low-magnification field lens 15B is more preferably a lens having a magnification of five times or less. When a lens having a magnification of five times or less is used, an image having a high field of view can be obtained. Thus, an image having wide coverage can be readily obtained.

The turret 16 is configured so as to be capable of switching to and selectively disposing in the predetermined position opposite the sample S any one of the plurality of indenter axes 14 (the first indenter axis 14A and the second indenter axis 14B) and the plurality of field lenses 15 (the high-magnification field lens 15A and the low-magnification field lens 15B), which are attached to the bottom surface of the turret 16, by rotating the turret 16 around a Z-axis direction. Specifically, the indentation can be formed in the surface of the sample S by disposing the indenter axes 14 in the predetermined position opposite the sample S, and the formed indentation can be observed by disposing the field lenses 15 in the predetermined position opposite the sample S. In other words, the turret 16 is a switcher capable of disposing one of the indenter axes 14 (the indenters 141) and the field lenses 15 in the predetermined position opposite the sample S.

The sample S is placed on an upper surface of the sample stage 2 and fixed in place with a sample holder 2a. The XY stage 3 is manually driven by a user and displaces the sample stage 2 in a direction (X-axis or Y-axis direction) perpendicular to a displacement direction (Z-axis direction) of the indenters 141 (i.e., in the horizontal direction). Specifically, the XY stage 3 is a horizontal stage displacer displacing the sample stage 2 in the horizontal direction. The elevator mechanism 5 is manually driven by the user and raises and lowers the sample stage 2 and the XY stage 3 in the Z-axis direction (i.e., the vertical direction), thereby changing a relative distance between the sample stage 2 and the field lenses 15.

The operator 7 is configured with a keyboard 71 and a mouse 72. The operator 7 executes an input operation by the user when performing a hardness test. In addition, when a predetermined input operation is performed by the operator 7, a predetermined operation signal corresponding to the input operation is output to the controller 6.

For example, the operator 7 enables the user to input a test condition value when carrying out the hardness test with the hardness tester 100. In addition, the input test condition value is sent to the controller 6. Herein, the test condition value is a value such as a material of the sample S, a test force (N) loaded on the sample S by the indenters 141, or a magnification power of the field lenses 15, for example.

The monitor 8 is configured with a display device such as an LCD, for example. The monitor 8 displays, for example, settings of the hardness test input on the operator 7, results of the hardness test, an image of the surface of the sample S and the indentation formed in the surface of the sample S captured by the CCD camera 12. Thus, the monitor 8 is a display.

Figure 4:
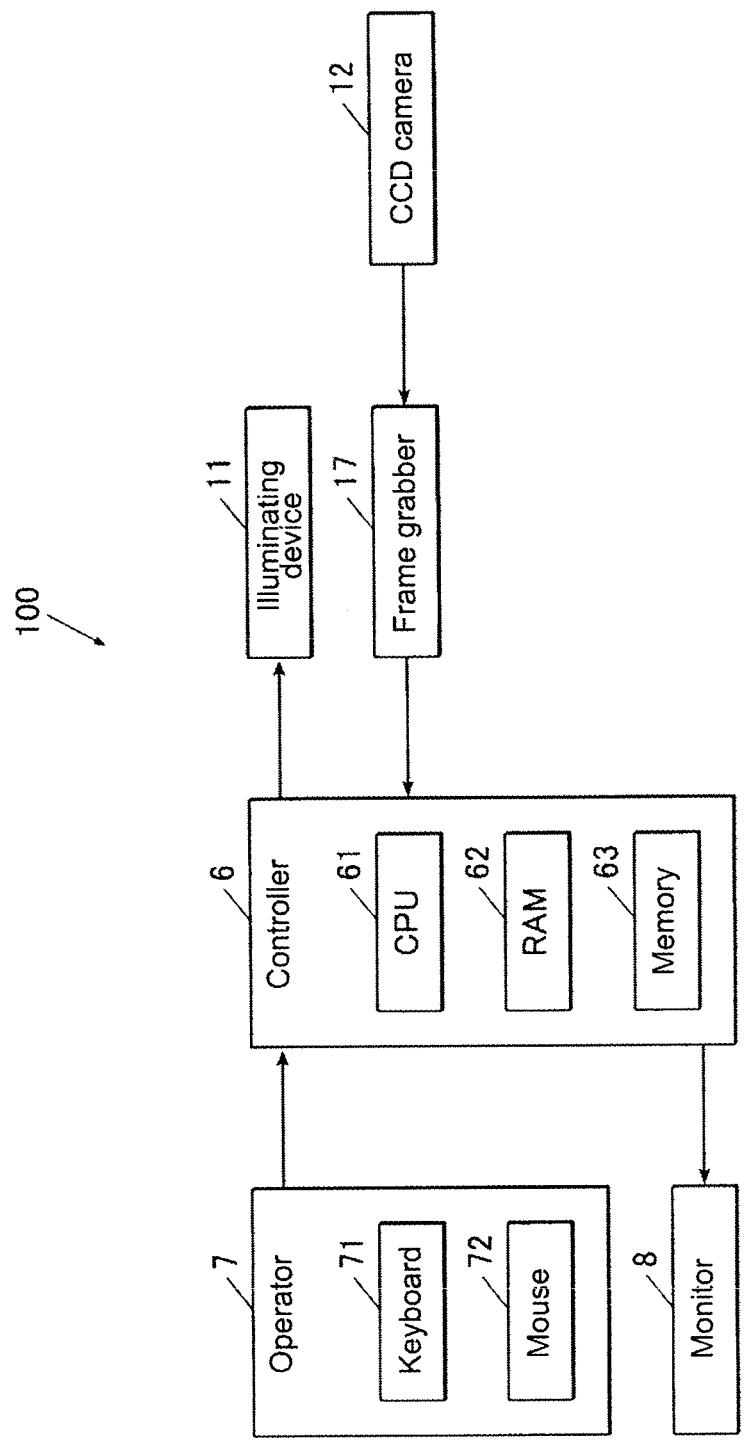
FIG. 4 is a block diagram illustrating a control structure of the hardness tester according to the first embodiment.

As shown in FIG. 4, the controller 6 is configured to include a CPU (Central Processing Unit) 61, a RAM (Random Access Memory) 62, and a memory 63. The controller 6 performs operation control for performing a predetermined hardness test by executing a predetermined program stored in the memory 63.

The CPU 61 retrieves a processing program stored in the memory 63, then opens and executes the processing program in the RAM 62. The CPU 61 thus performs overall control of the hardness tester 100.

The RAM 62 opens the processing program executed by the CPU 61 in a program storage region within the RAM 62 and stores input data and processing results generated when the processing program is executed in a data storage region.

The memory 63 includes, for example, a recording medium (not shown in the drawings) storing a program, data, and the like. The recording medium is configured with a semiconductor memory and the like. In addition, the memory 63 stores various kinds of data, various kinds of processing programs, and data processed by running the programs that allow the CPU 61 to perform overall control of the hardness tester 100. The memory 63 also stores correction parameters such as an amount of offset in the horizontal direction between the center position of the first indenter 141A when disposed in the predetermined position opposite the sample S and the center position of the second indenter 141B when disposed in the predetermined position; the amount of offset in the horizontal direction between the center position of the first indenter 141A when disposed in the predetermined position opposite the sample S and the center position of the low-magnification field lens 15B when disposed in the predetermined position; and the amount of offset in the horizontal direction between the center position of the first indenter 141A when disposed in the predetermined position opposite the sample S and the center position of the high-magnification field lens 15A when disposed in the predetermined position. Thus, the memory 63 is a memory.

Figure 5:
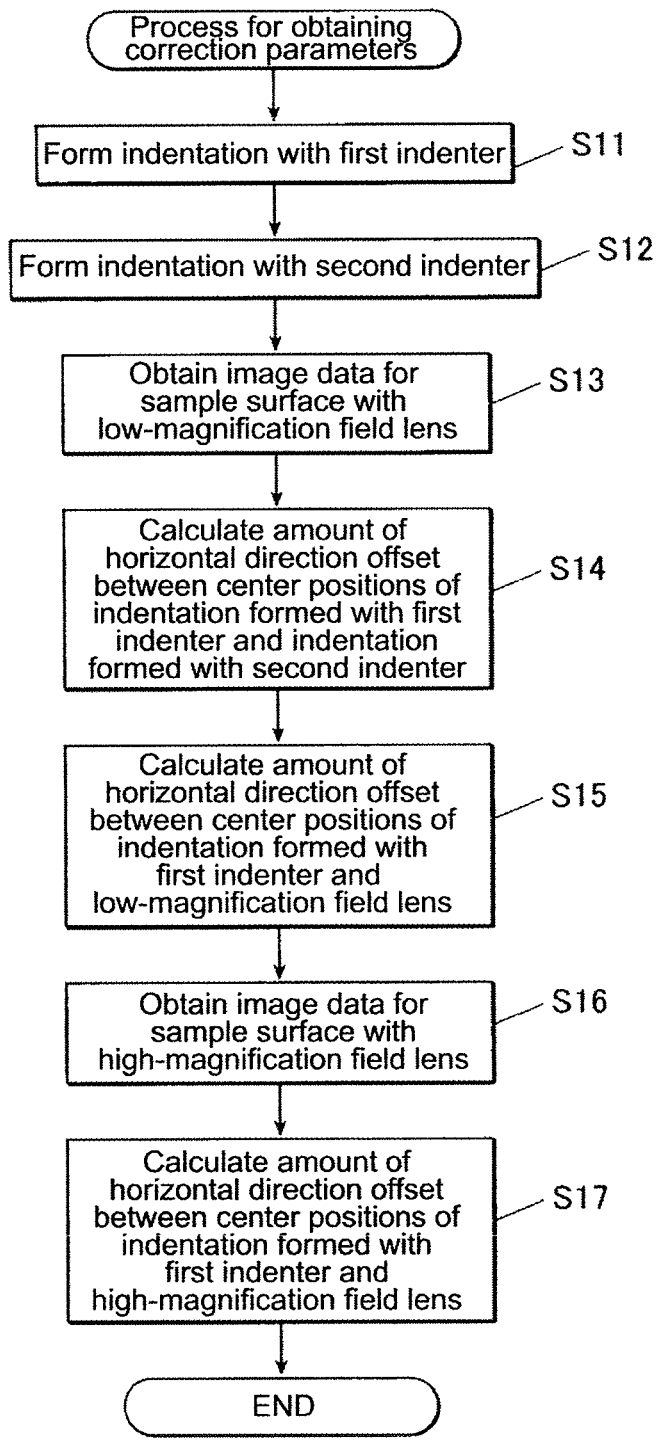
FIG. 5 is a flow chart illustrating a process for obtaining correction parameters in the hardness tester according to the first embodiment.

Next, operations of the hardness tester 100 according to the first embodiment are described. First, a process for obtaining correction parameters performed in an early stage of the hardness test in the hardness tester 100 according to the first embodiment is described with reference to a flow chart in FIG. 5.

Figure 6:
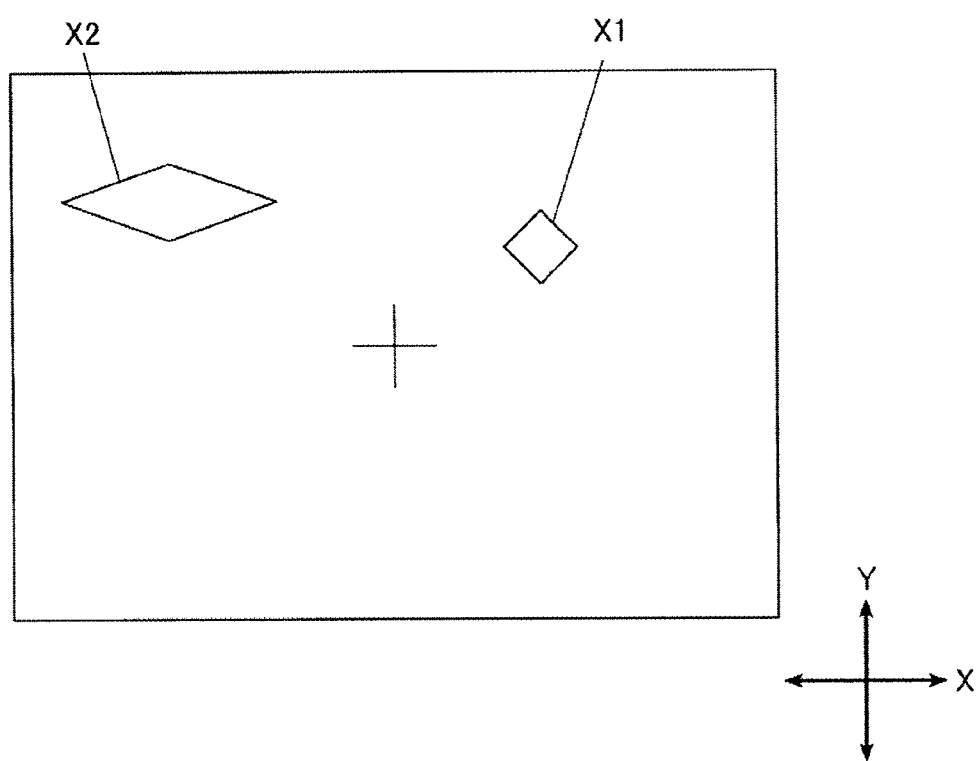
FIG. 6 illustrates an example of indentations formed by each indenter in a surface of a sample using the process for obtaining correction parameters.

First, the indentation is formed in the surface of the sample S by the first indenter 141A (step S11). Specifically, the user places the sample S undergoing the hardness test on the sample stage 2 and fixes the sample S in place with the sample holder 2a. The user then rotates the turret 16 to dispose the first indenter 141A in the predetermined position opposite the sample S, then operates the operator 7 to input an indentation instruction. When the CPU 61 receives the operation signal corresponding to the input operation from the operator 7, the load mechanism (not shown in the drawings) is driven, thereby lowering the first indenter 141A and forming an indentation X1 in the surface of the sample S (see FIG. 6).

Next, an indentation is formed in the surface of the sample S by the second indenter 141B (step S12). Specifically, the user rotates the turret 16 to dispose the second indenter 141B in the predetermined position opposite the sample S, then operates the operator 7 to input the indentation instruction. When the CPU 61 receives the operation signal corresponding to the input operation from the operator 7, the load mechanism (not shown in the drawings) is driven, thereby lowering the second indenter 141B and forming an indentation X2 in the surface of the sample S (see FIG. 6).

Next, image data for the surface of the sample S is obtained by the low-magnification field lens 15B (step S13). Specifically, the user rotates the turret 16 to dispose the low-magnification field lens 15B in the predetermined position opposite the sample S. The CCD camera 12 captures an image of the surface of the sample S via the low-magnification field lens 15B to obtain the image data, then outputs the image data to the controller 6.

Figure 7:
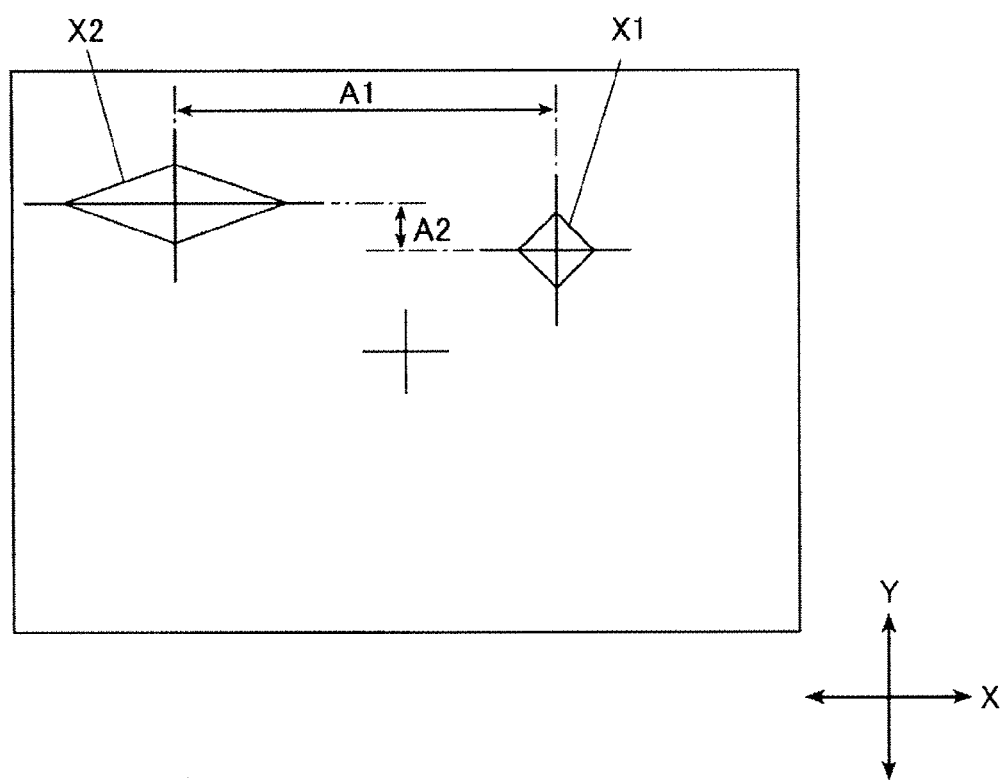
FIG. 7 is an explanatory diagram describing an amount of offset in an XY direction between a center position of an indentation formed by a first indenter and the center position of an indentation formed by a second indenter.

Next, the amount of offset in the horizontal direction between the center position of the indentation X1, formed by the first indenter 141A, and the center position of the indentation X2, formed by the second indenter 141B, is calculated (step S14). Specifically, the CPU 61 analyzes the image data for the surface of the sample S output from the CCD camera 12. The CPU 61 then calculates an amount of offset A1 in the X direction and an amount of offset A2 in the Y direction between the center position of the indentation X1, formed by the first indenter 141A, and the center position of the indentation X2, formed by the second indenter 141B (see FIG. 7). The CPU 61 then stores the amounts of offset A1 and A2 in the memory 63 as correction parameters. The correction parameters are the amount of offset in the horizontal direction between the center position of the first indenter 141A when disposed in the predetermined position opposite the sample S and the center position of the second indenter 141B when disposed in the predetermined position.

Figure 8:
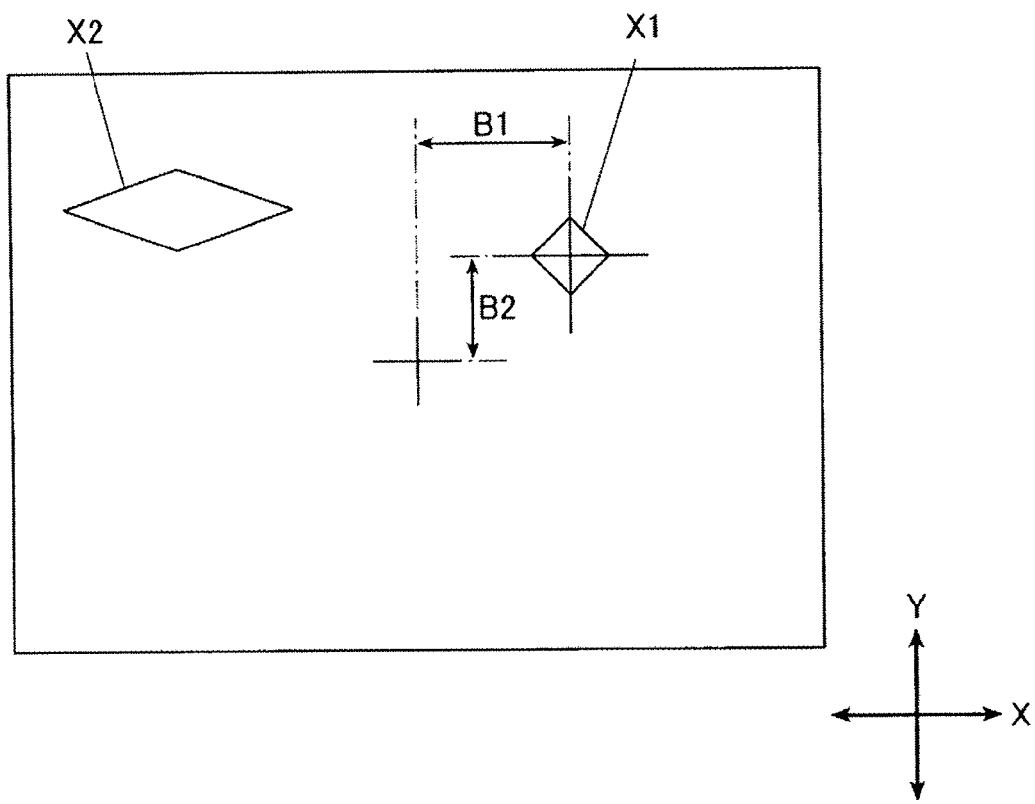
FIG. 8 is an explanatory diagram describing the amount of offset in the XY direction between the center position of the indentation formed by the first indenter and the center position of a low-magnification field lens.

Next, the amount of offset in the horizontal direction between the center position of the indentation X1, formed by the first indenter 141A, and the center position of the low-magnification field lens 15B is calculated (step S15). Specifically, the CPU 61 analyzes the image data for the surface of the sample S output from the CCD camera 12. The CPU 61 then calculates an amount of offset B1 in the X direction and an amount of offset B2 in the Y direction between the center position of the indentation X1 formed by the first indenter 141A and the center position of the low-magnification field lens 15B (see FIG. 8). The CPU 61 then stores the amounts of offset B1 and B2 in the memory 63 as the correction parameters. The correction parameters are the amount of offset in the horizontal direction between the center position of the first indenter 141A when disposed in the predetermined position opposite the sample S and the center position of the low-magnification field lens 15B when disposed in the predetermined position.

Next, the image data of the surface of the sample S is obtained by the high-magnification field lens 15A (step S16). Specifically, the user rotates the turret 16 to dispose the high-magnification field lens 15A in the predetermined position opposite the sample S. The CCD camera 12 captures an image of the surface of the sample S via the high-magnification field lens 15A to obtain the image data, then outputs the image data to the controller 6.

Next, the amount of offset in the horizontal direction between the center position of the indentation X1, formed by the first indenter 141A, and the center position of the high-magnification field lens 15A is calculated (step S17). Specifically, the CPU 61 analyzes the image data for the surface of the sample S output from the CCD camera 12. The CPU 61 then calculates the amount of offset in the X direction and the amount of offset in the Y direction (not shown in the drawings) between the center position of the indentation X1, formed by the first indenter 141A, and the center position of the high-magnification field lens 15A. The CPU 61 then stores the amounts of offset in the memory 63 as the correction parameters. The correction parameters are the amount of offset in the horizontal direction between the center position of the first indenter 141A when disposed in the predetermined position opposite the sample S and the center position of the high-magnification field lens 15A when disposed in the predetermined position.

In the first embodiment described above, with the center position of the first indenter 141A as a reference, the amount of offset is calculated in order of the amount of offset in the horizontal direction with the center position of the second indenter 141B (step S14), the amount of offset in the horizontal direction with the center position of the low-magnification field lens 15B (step S15), and the amount of offset in the horizontal direction with the center position of the high-magnification field lens 15A (step S17). However, the order of calculating the amounts of offset is not particularly limited and may be calculated in any order. In addition, with the center position of the second indenter 141B as the reference, the amount of offset in the horizontal direction with the center position of the first indenter 141A, the amount of offset in the horizontal direction with the center position of the low-magnification field lens 15B, and the amount of offset in the horizontal direction with the high-magnification field lens 15A may be calculated and then stored in the memory 63.

Figure 9:
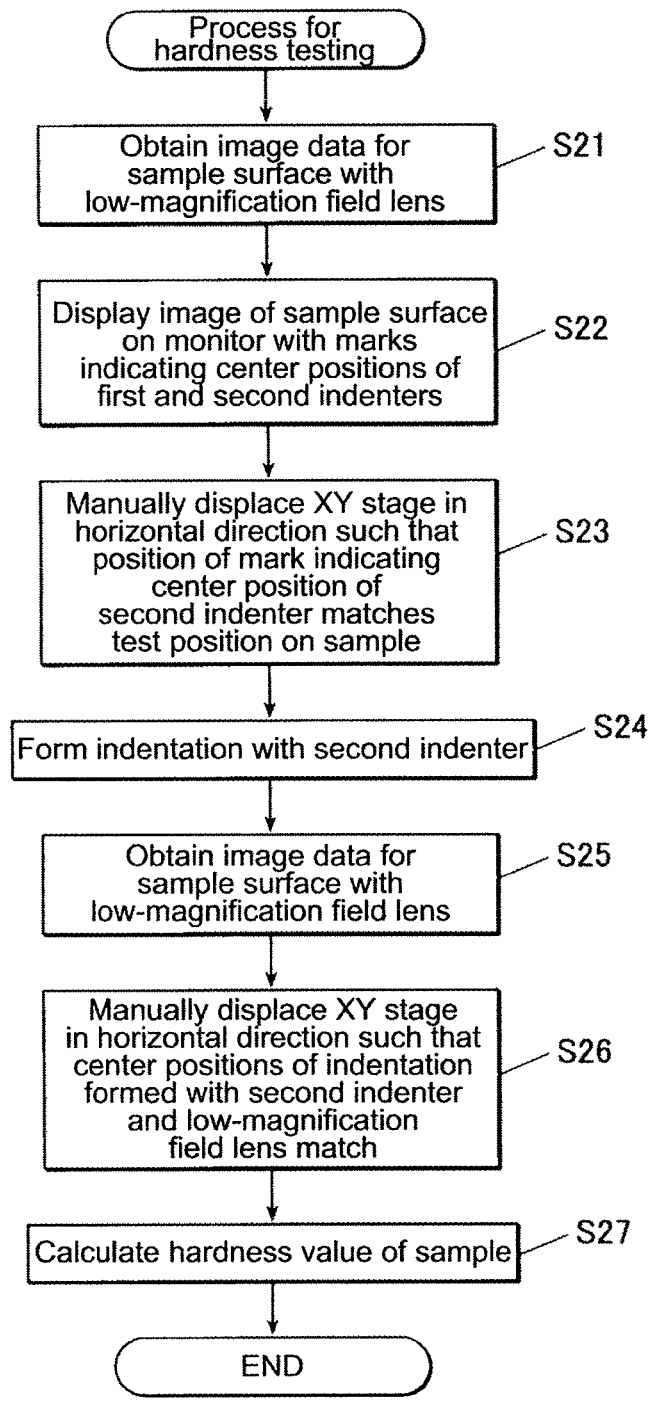
FIG. 9 is a flow chart illustrating a process for hardness testing in the hardness tester according to the first embodiment.

Next, a process for hardness testing in the hardness tester 100 according to the first embodiment is described with reference to a flow chart in FIG. 9. Herein, an exemplary case is described in which the hardness test is performed using the second indenter 141B.

First, the image data for the surface of the sample S is obtained by the low-magnification field lens 15B (step S21). Specifically, the user rotates the turret 16 to dispose the low-magnification field lens 15B in the predetermined position opposite the sample S. Herein, the low-magnification field lens 15B is disposed in the predetermined position opposite the sample S; however, the high-magnification field lens 15A may also be disposed. The CCD camera 12 captures an image of the surface of the sample S via the low-magnification field lens 15B to obtain the image data, then outputs the image data to the controller 6.

Figure 10:
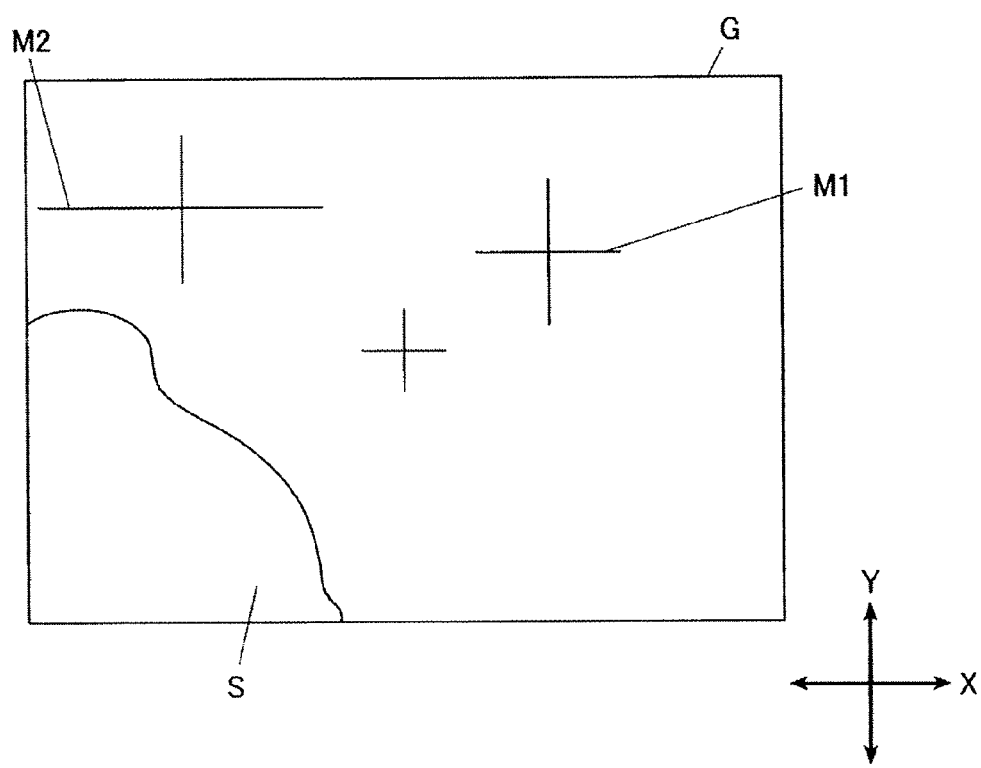
FIG. 10 illustrates an example of marks indicating the center position of each indenter displayed on a monitor in the process for hardness testing.

Next, the image of the surface of the sample S is displayed on the monitor 8 with a mark indicating the center position of the first indenter 141A and a mark indicating the center position of the second indenter 141B (step S22). Specifically, the CPU 61 displays an image G of the surface of the sample S on the monitor 8 based on the image data for the surface of the sample S output from the CCD camera 12 (see FIG. 10). At this point, the CPU 61 references the correction parameters stored in the memory 63, then displays a mark M1 and a mark M2 on the image G. The mark M1 indicates the center position of the first indenter 141A when disposed in the predetermined position opposite the sample S. The mark M2 indicates the center position of the second indenter 141B when disposed in the predetermined position opposite the sample S. Specifically, the CPU 61 references the amount of offset in the horizontal direction between the center position of the first indenter 141A and the center point of the low-magnification field lens 15B to calculate and display a display position of the mark M1. The CPU 61 also references the amount of offset in the horizontal direction between the center position of the first indenter 141A and the center position of the second indenter 141B to calculate and display the display position of the mark M2. In other words, when the field lenses 15 are disposed in the predetermined position by the turret 16, the CPU 61 is a display controller displaying the marks M1 and M2 indicating the center positions of the indenters 141 (the first indenter 141A and the second indenter 141B) on the monitor 8 based on the amount of offset stored in the memory 63. In this way, by displaying the marks M1 and M2 indicating the center position of each indenter 141, the user can recognize planned positions for indentation formation before the indentations are formed by each of the indenters 141. In the first embodiment described above, the marks M1 and M2 indicating the center positions of the indenters 141 (the first indenter 141A and the second indenter 141B) are displayed on the monitor 8. However, in addition, the amount of offset in the horizontal direction between the center position of the first indenter 141A and the center position of the low-magnification field lens 15B as well as the amount of offset in the horizontal direction between the center position of the second indenter 141B and the center position of the low-magnification field lens 15B can also be displayed in a desired position on the screen of the monitor 8. When the high-magnification field lens 15A is selected in step S21, the amount of offset in the horizontal direction between the center positions of each of the indenters 141 (the first indenter 141A and the second indenter 141B) and the center position of the high-magnification field lens 15A is displayed.

Figure 11:
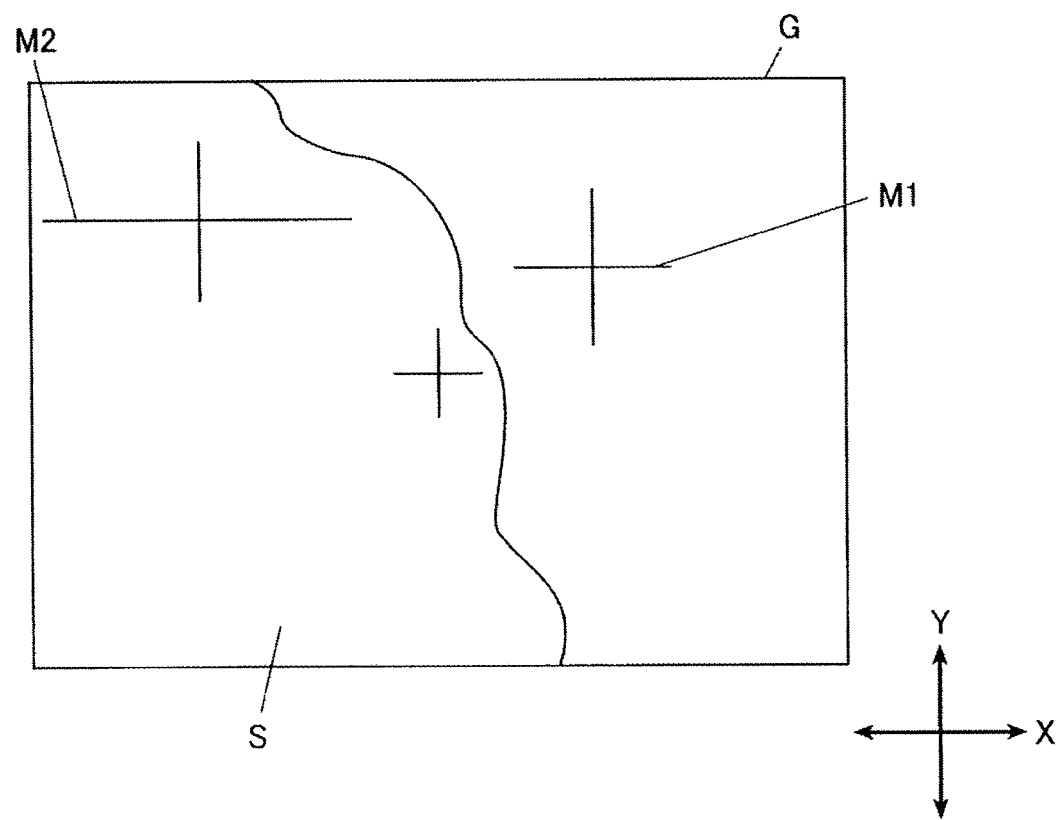
FIG. 11 illustrates an example of a sample displaced from the state of FIG. 10 such that a position of the mark indicating the center position of the second indenter matches a test position on the sample.

Next, the XY stage 3 is manually displaced in the horizontal direction such that the position of the mark M2, indicating the center position of the second indenter 141B, matches the test position on the sample S (step S23). Specifically, the user manually displaces the XY stage 3 in the horizontal direction such that the position of the mark M2, indicating the center position of the second indenter 141B, matches the test position (i.e., a position where the user wishes to form the indentation) on the sample S (see FIG. 11).

Figure 12:
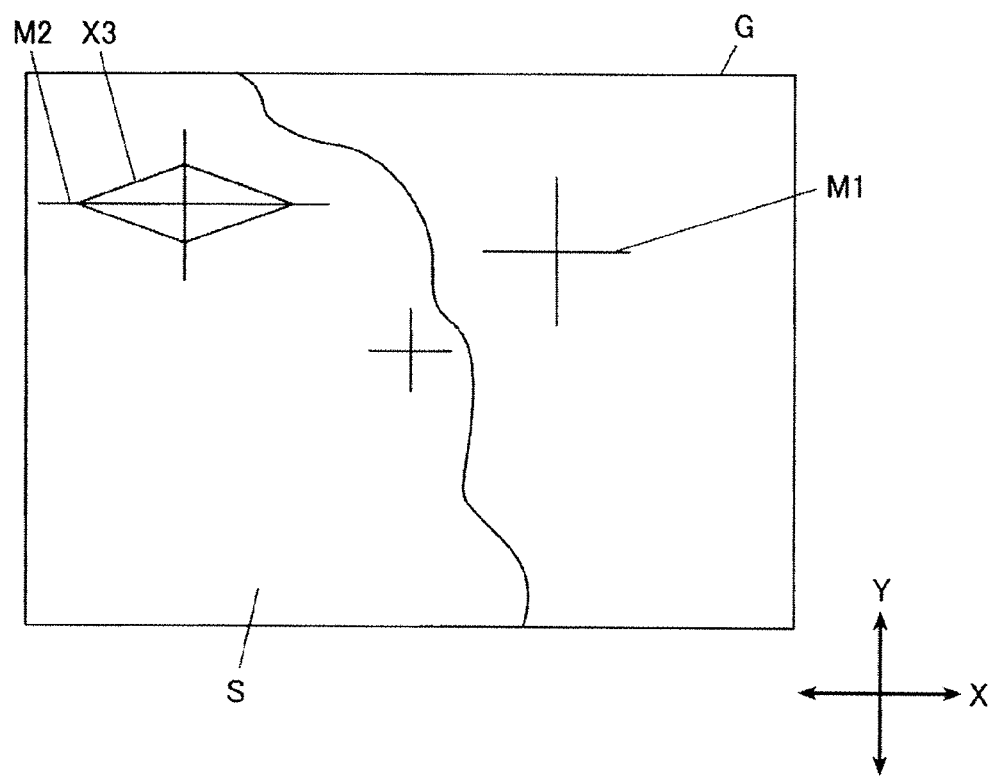
FIG. 12 illustrates an example of the indentation formed by the second indenter, from the state in FIG. 11.

Next, the indentation is formed in the surface of the sample S by the second indenter 141B (step S24). Specifically, the user rotates the turret 16 to dispose the second indenter 141B in the predetermined position opposite the sample S, then operates the operator 7 to input the indentation instruction. When the CPU 61 receives the operation signal corresponding to the input operation from the operator 7, the load mechanism (not shown in the drawings) is driven, thereby lowering the second indenter 141B and forming an indentation X3 in the surface of the sample S (see FIG. 12).

Next, the image data for the surface of the sample S is obtained by the low-magnification field lens 15B (step S25). Specifically, the user rotates the turret 16 to dispose the low-magnification field lens 15B in the predetermined position opposite the sample S. Herein, the low-magnification field lens 15B is disposed in the predetermined position opposite the sample S; however, the high-magnification field lens 15A may also be disposed. The CCD camera 12 captures an image of the surface of the sample S via the low-magnification field lens 15B to obtain the image data, then outputs the image data to the controller 6.

Next, the XY stage 3 is manually displaced in the horizontal direction such that the center position of the indentation X3, formed by the second indenter 141B in step S24, matches the center position of the low-magnification field lens 15B (step S26). Specifically, the CPU 61 displays the image G of the surface of the sample S on the monitor 8 based on the image data for the surface of the sample S output from the CCD camera 12 (see FIG. 12). The user references the image G displayed on the monitor 8 to manually displace the XY stage 3 in the horizontal direction such that the center position of the indentation X3 matches the center position of the low-magnification field lens 15B.

Next, a hardness value for the sample S is calculated based on the indentation X3 formed in the surface of the sample S (step S27). Specifically, the CPU 61 analyzes the image data for the surface of the sample S output from the CCD camera 12, then measures a length of diagonal lines in the indentation X3 formed in the surface of the sample S. The CPU 61 then calculates the hardness value for the sample S based on the measured length of the diagonal lines.

As described above, the hardness tester 100 according to the first embodiment includes the XY stage 3 displacing the sample stage 2 in the horizontal direction; the CCD camera 12 capturing images of the surface of the sample S via the field lenses 15; the monitor 8 displaying the image of the surface of the sample S captured by the CCD camera 12; the turret 16 capable of selectively disposing one of the indenters 141 and the field lenses 15 in the predetermined position opposite the sample S; the memory 63 storing the amount of offset in the horizontal direction between the center positions of the indenters 141 when disposed in the predetermined position and the center positions of the field lenses 15 when disposed in the predetermined position; and the CPU 61 displaying, based on the amount of offset stored in the memory 63, the marks M1 and M2 when the field lenses 15 are disposed in the predetermined position by the turret 16, the marks M1 and M2 indicating the center positions of the indenters 141 on the monitor 8. Therefore, the planned position for indentation formation can be recognized before the indentation is formed by the indenters 141. Thus, even when the center positions of the indenters 141 and the center positions of the field lenses 15 are offset, the user can form the indentation in the desired test position and an accurate hardness test can be performed.

According to the hardness tester 100 according to the first embodiment, the indenters 141 include the first indenter 141A and the second indenter 141B. The memory 63 stores the amount of offset in the horizontal direction between the center position of the first indenter 141A when disposed in the predetermined position and the center position of the second indenter 141B when disposed in the predetermined position. When the field lenses 15 are disposed in the predetermined position by the turret 16, the CPU 61 displays the marks M1 and M2, indicating the center position of the first indenter 141A and the center position of the second indenter 141B, on the monitor 8 based on the amount of offset stored in the memory 63. Therefore, when two indenters 141 are provided, offset between the indenters 141 in the horizontal direction and offset in the horizontal direction between each of the indenters 141 and the field lenses 15 can be corrected. Thus, even when two indenters 141 are provided, the user can form the indentation in the desired test position and an accurate hardness test can be performed.

Second Embodiment

Figure 13:
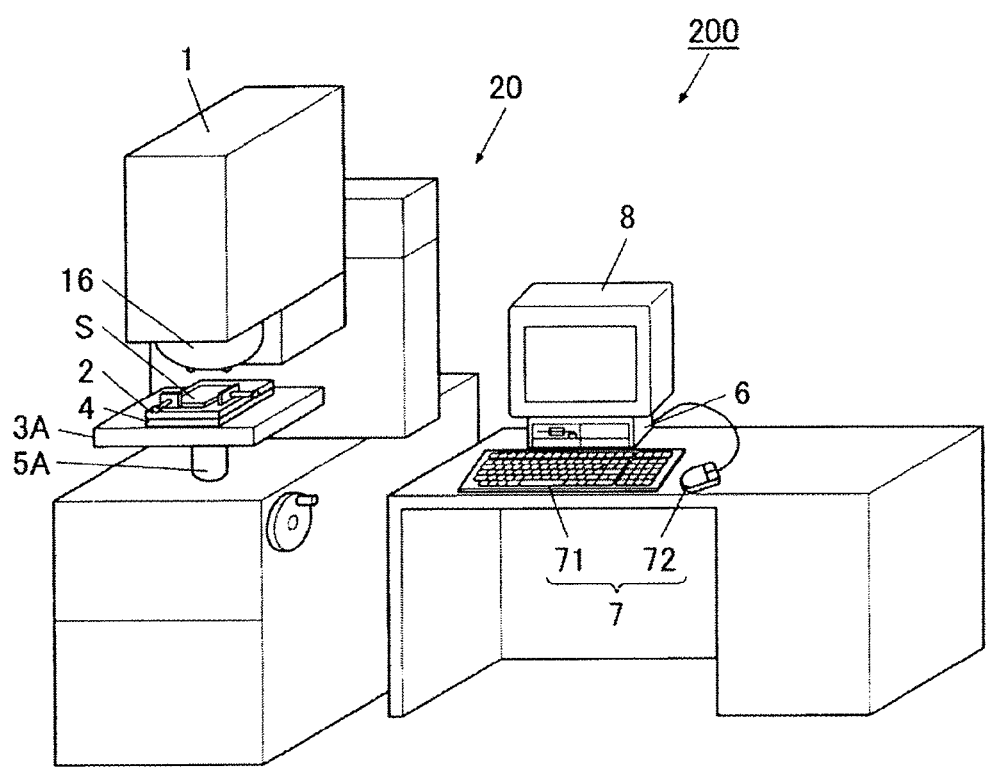
FIG. 13 is a perspective view illustrating an overall configuration of a hardness tester according to a second embodiment.
Figure 14:
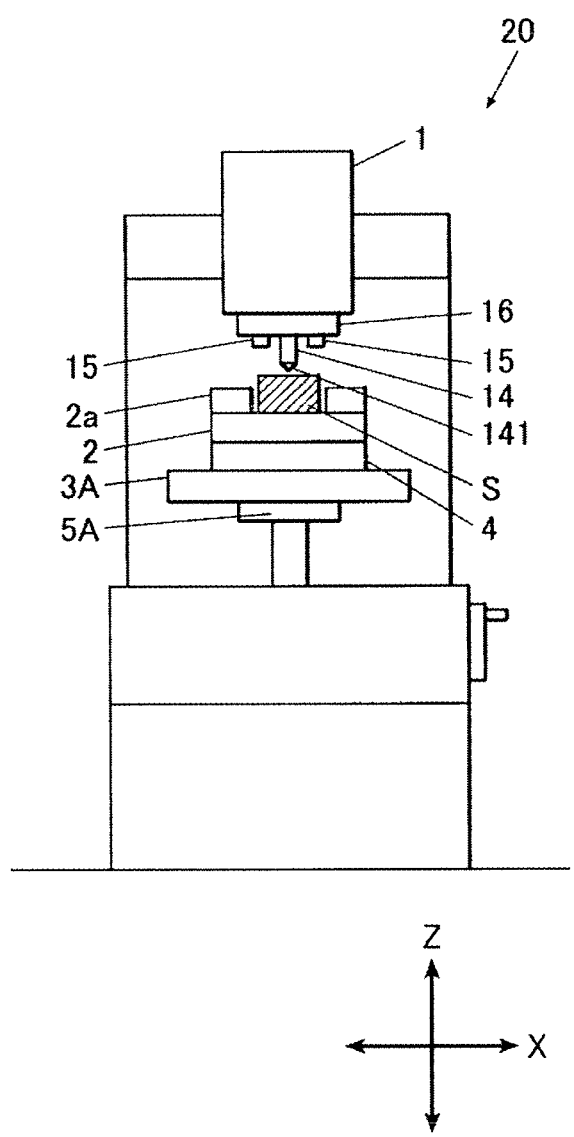
FIG. 14 is a schematic view illustrating a hardness tester main body of the hardness tester according to the second embodiment.
Figure 15:
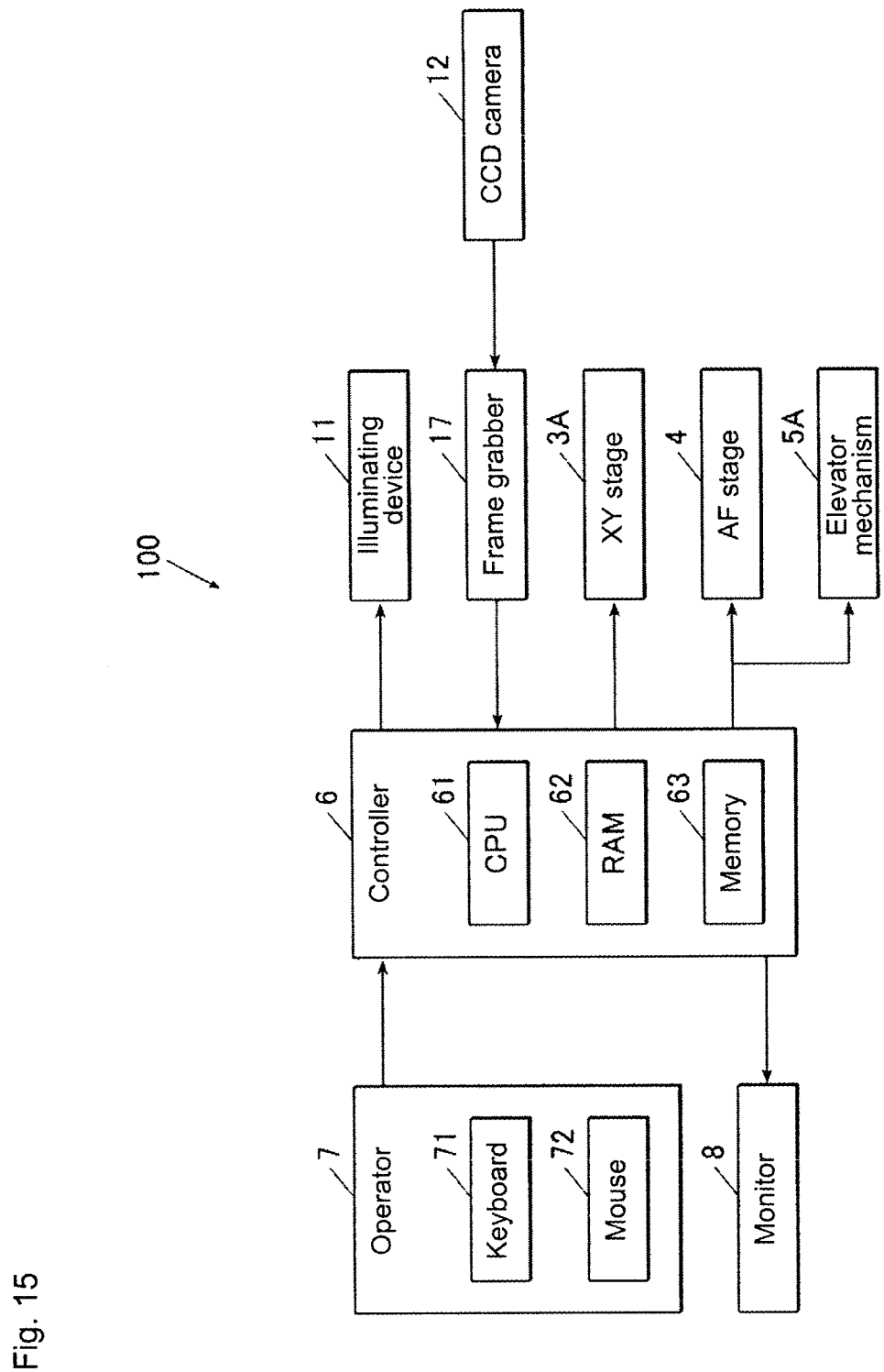
FIG. 15 is a block diagram illustrating a control structure of the hardness tester according to the second embodiment.

A hardness tester 200 according to a second embodiment is a hardness tester that includes an automatic XY stage 3A and, as shown in FIGS. 13 and 14, includes a tester main body 20, the controller 6, the operator 7, and the monitor 8. Moreover, in order to simplify the description, identical reference numerals are used for structures similar to those in the first embodiment and a detailed description thereof is omitted.

The tester main body 20 includes the hardness measurer 1 performing the measurement of the hardness of the sample S; the sample stage 2 on which the sample S is placed; the XY stage 3A displacing the sample stage 2; the AF stage 4 to focus on the surface of the sample S; and an elevator mechanism 5A raising and lowering the sample stage 2 (the XY stage 3A and the AF stage 4).

The XY stage 3A is driven by the drive mechanism (not shown in the drawings) driven in response to the control signal output by the controller 6. The XY stage 3A then displaces the sample stage 2 in a direction (X-axis and Y-axis directions) perpendicular to the displacement direction (Z-axis direction) of the indenter 141 (i.e., the horizontal direction). Specifically, the XY stage 3A is the horizontal stage displacer displacing the sample stage 2 in the horizontal direction. The AF stage 4 is driven in response to the control signal output by the controller 6. The AF stage 4 then minutely raises and lowers the sample stage 2 based on the image data captured by the CCD camera 12 to focus on the surface of the sample S. The elevator mechanism 5A is driven in response to the control signal output by the controller 6. The elevator mechanism 5A then raises and lowers the sample stage 2 (the XY stage 3A and the AF stage 4) in the Z-axis direction (i.e., the vertical direction), thereby changing the relative distance between the sample stage 2 and the field lens 15. Specifically, the AF stage 4 and the elevator mechanism 5A are a stage elevator raising and lowering the sample stage 2 in the vertical direction.

Figure 16:
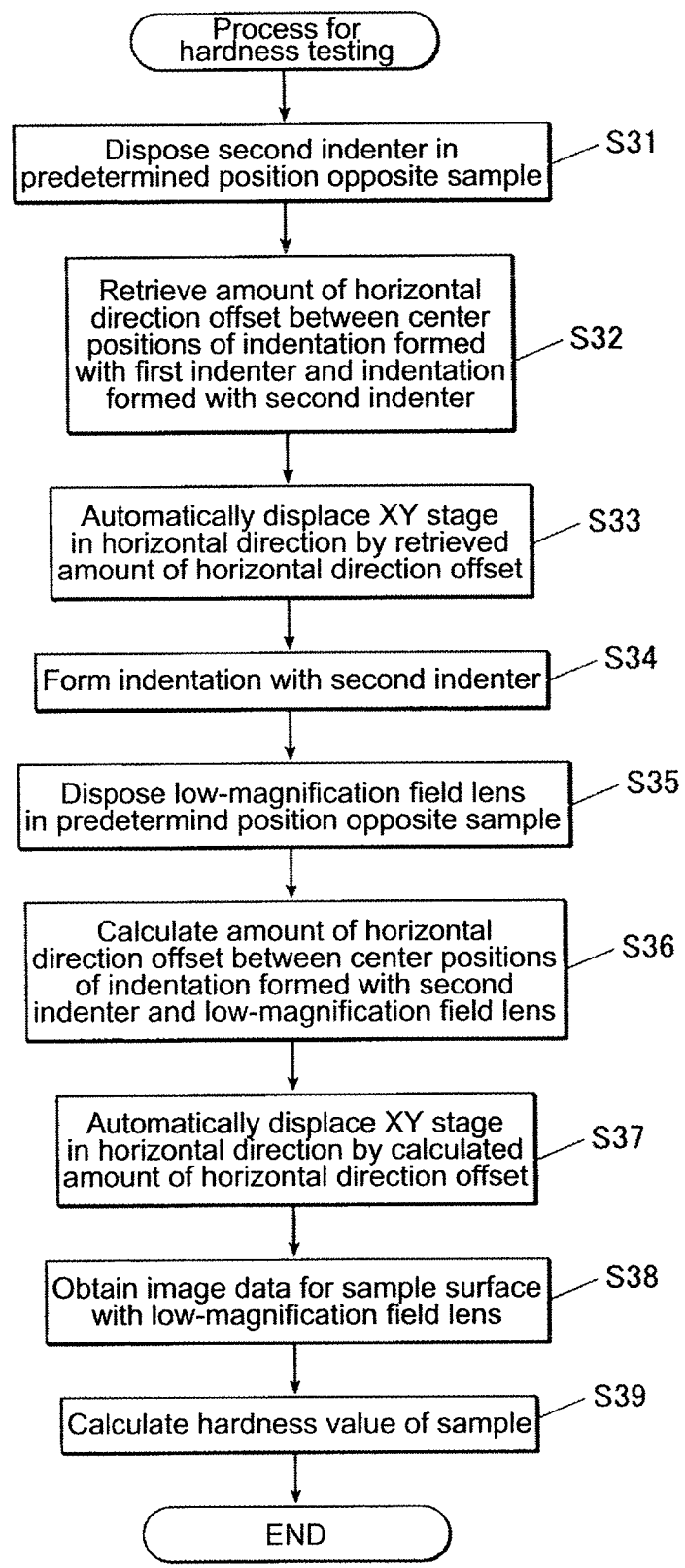
FIG. 16 is a flow chart illustrating a process for hardness testing in the hardness tester according to the second embodiment.

Next, operations of the hardness tester 200 according to the second embodiment are described. The process for obtaining the correction parameters in the hardness tester 200 is similar to the process in the hardness tester 100 according to the first embodiment and a description thereof is thus omitted. A process for hardness testing in the hardness tester 200 is described with reference to a flow chart in FIG. 16. Herein, similar to the process for hardness testing in the hardness tester 100, an exemplary case is described in which the hardness test is performed using the second indenter 141B. In addition, in a stage prior to the process, the first indenter 141A is disposed in the predetermined position opposite the sample S.

First, the second indenter 141B is disposed in the predetermined position opposite the sample S (step S31). Specifically, the user rotates the turret 16 to dispose the second indenter 141B in the predetermined position opposite the sample S.

Next, the CPU 61 references the correction parameters and retrieves the amount of offset in the horizontal direction between the center position of the indentation X1, formed by the first indenter 141A, and the center position of the indentation X2, formed by the second indenter 141B (step S32). Specifically, the CPU 61 references the correction parameters stored in the memory 63, then retrieves the amount of offset A1 in the X direction and the amount of offset A2 in the Y direction between the center position of the indentation X1, formed by the first indenter 141A, and the center position of the indentation X2, formed by the second indenter 141B. In other words, the CPU 61 retrieves the amount of offset in the XY direction (i.e., the horizontal direction) between the center position of the first indenter 141A when disposed in the predetermined position before rotating the turret 16 and the center position of the second indenter 141B when disposed in the predetermined position after rotating the turret 16.

Next, the XY stage 3A is automatically displaced in the horizontal direction by the amount of offset in the horizontal direction retrieved in step S32 (step S33). Specifically, the CPU 61 automatically displaces the XY stage 3A in the horizontal direction by the retrieved amount of offset A1 in the X direction and the amount of offset A2 in the Y direction. Accordingly, the offset in the horizontal direction between the center position of the first indenter 141A and the center position of the second indenter 141B is corrected. Specifically, the CPU 61 is the stage displacement controller displacing the XY stage 3A to a position corresponding to the center position of the second indenter 141B when disposed in the predetermined position by the turret 16, based on the amount of offset stored in the memory 63.

Next, the indentation is formed in the surface of the sample S by the second indenter 141B (step S34). Specifically, the user operates the operator 7 to input the indentation instruction. When the CPU 61 receives the operation signal corresponding to the input operation from the operator 7, the load mechanism (not shown in the drawings) is driven, thereby lowering the second indenter 141B and forming the indentation in the surface of the sample S.

Next, the low-magnification field lens 15B is disposed in the predetermined position opposite the sample S (step S35). Specifically, the user rotates the turret 16 to dispose the low-magnification field lens 15B in the predetermined position opposite the sample S. Herein, the low-magnification field lens 15B is disposed in the predetermined position opposite the sample S; however, the high-magnification field lens 15A may also be disposed.

Next, the CPU 61 references the correction parameters to calculate the amount of offset in the horizontal direction between the center position of the indentation X2, formed by the second indenter 141B, and the center position of the low-magnification field lens 15B (step S36). Specifically, the CPU 61 references the correction parameters stored in the memory 63, then retrieves the amount of offset B1 in the X direction and the amount of offset B2 in the Y direction between the center position of the indentation X1, formed by the first indentater 141A, and the center position of the low-magnification field lens 15B. Then, the amount of offset A1 in the X direction and the amount of offset A2 in the Y direction (between the center position of the indentation X1, formed by the first indenter 141A, and the center position of the indentation X2, formed by the second indenter 141B) are referenced in combination, the amounts of offset A1 and A2 having been retrieved previously in step S32. Thereby, the amount of offset in the XY direction (i.e., the horizontal direction) between the center position of the second indenter 141B when disposed in the predetermined position before rotating the turret 16 and the center position of the low-magnification field lens 15B when disposed in the predetermined position after rotating the turret 16 is calculated using the center position of the first indenter 141A.

Next, the XY stage 3A is automatically displaced in the horizontal direction by the amount of offset in the horizontal direction calculated in step S36 (step S37). Specifically, the CPU 61 automatically displaces the XY stage 3A in the horizontal direction by the amount of offset in the horizontal direction between the center position of the second indenter 141B and the center position of the low-magnification field lens 15B. Thereby, the offset in the horizontal direction between the center position of the second indenter 141B and the center position of the low-magnification field lens 15B is corrected. Specifically, the CPU 61 is the stage displacement controller displacing the XY stage 3A to a position corresponding to the center position of the field lenses 15 (the low-magnification field lens 15B) when disposed in the predetermined position by the turret 16.

Next, the image data for the surface of the sample S is obtained by the low-magnification field lens 15B (step S38). Specifically, the CCD camera 12 captures an image of the surface of the sample S via the low-magnification field lens 15B to obtain the image data, then outputs the image data to the controller 6.

Next, the hardness value of the sample S is calculated based on the indentation formed in the surface of the sample S in step S34 (step S39). Specifically, the CPU 61 analyzes the image data for the surface of the sample S output from the CCD camera 12 to measure the length of the diagonal lines of the indentation formed in the surface of the sample S, then calculates the hardness value of the sample S based on the measured length of the diagonal lines.

As described above, the hardness tester 200 according to the second embodiment includes the XY stage 3A displacing the sample stage 2 in the horizontal direction; the CCD camera 12 capturing the image of the surface of the sample S via the field lenses 15; the turret 16 capable of selectively disposing one of the indenters 141 and the field lenses 15 in the predetermined position opposite the sample S; the memory 63 storing the amount of offset in the horizontal direction between the center position of the indenters 141 when disposed in the predetermined position and the center position of the field lenses 15 when disposed in the predetermined position; and the CPU 61 disposing the XY stage 3A to the position corresponding to the center position of one of the indenters 141 and the field lenses 15 when disposed in the predetermined position by the turret 16, based on the amount of offset stored in the memory 63. Therefore, the XY stage 3A is automatically displaced to the position corresponding to the center position of the indenters 141 during formation of the indentation by the indenters 141. Thus, even when the center position of the indenters 141 and the center position of the field lenses 15 are offset, the user can form the indentation in the desired test position and an accurate hardness test can be performed.

According to the hardness tester 200 according to the second embodiment, the indenters 141 include the first indenter 141A and the second indenter 141B. The memory 63 stores the amount of offset in the horizontal direction between the center position of the first indenter 141A when disposed in the predetermined position and the center position of the second indenter 141B when disposed in the predetermined position. Based on the amount of offset stored in the memory 63, the CPU 61 displaces the XY stage 3A to the position corresponding to the center position of one of the first indenter 141A, the second indenter 141B, and the field lens 15, which is disposed in the predetermined position by the turret 16. Therefore, when two indenters 141 are provided, offset in the horizontal direction between the indenters 141 and offset in the horizontal direction between each of the indenters 141 and the field lenses 15 can be corrected. Thus, even when two indenters 141 are provided, the user can form the indentation in the desired test position and an accurate hardness test can be performed.

First Modification Example

The hardness tester 200 according to the second embodiment, described above, corrects only the offset in the XY direction (i.e., the horizontal direction) between the center position of one of the indenters 141 and the field lenses 15, which is disposed in the predetermined position before rotating the turret 16, and the center position of one of the indenters 141 and the field lenses 15, which is disposed in the predetermined position after rotating the turret 16. However, offset in the Z direction (i.e., the vertical direction) can also be corrected.

Specifically, the hardness tester 200 according to a first modification example can correct offset in the vertical direction by using a position (height) of the sample stage 2 when indentation is performed by one of the first indenter 141A and the second indenter 141B as a reference position; calculating, in the process for obtaining the correction parameters, the amount of offset in the vertical direction between the reference position and a position (height) of the sample stage 2 when each of the field lenses 15 is focused; and, in the process for hardness testing, raising and lowering the position of the sample stage 2 based on the amount of offset in the vertical direction.

Specifically, first, before the process for obtaining the correction parameters, the position of the sample stage 2 when indentation is performed by one of the first indenter 141A and the second indenter 141B is pre-stored in the memory 63 as the reference position.

Then, in step S13 of the process for obtaining the correction parameters (see FIG. 5), when the low-magnification field lens 15B is disposed in the predetermined position opposite the sample S by the user, the CPU 61 raises and lowers the AF stage 4 to perform automatic focusing on the surface of the sample S based on the image data for the surface of the sample S obtained by the CCD camera 12. Next, the CPU 61 calculates the position of the sample stage 2 when the automatic focusing has the low-magnification field lens 15B in focus and calculates the amount of offset in the vertical direction from the reference position stored in the memory 63. The CPU 61 then stores the amount of offset in the memory 63 as the correction parameter. The correction parameter is the amount of offset in the vertical direction between the position of the sample stage 2 when formation of the indentation is performed by one of the first indenter 141A and the second indenter 141B, which is disposed in the predetermined position opposite the sample S, and the position of the sample stage 2 when the low-magnification field lens 15B, which is disposed in the predetermined position, is focused. The automatic focusing and obtaining the amount of offset in the vertical direction may be performed at any time as long as the automatic focusing and obtaining the amount of offset in the vertical direction are performed after performing the process of step S13 and before proceeding to step S16 in the process for obtaining the correction parameters.

Next, in step S16 of the process for obtaining the correction parameters, when the high-magnification field lens 15A is disposed in the predetermined position opposite the sample S by the user, the CPU 61 raises and lowers the AF stage 4 to perform automatic focusing on the surface of the sample S based on the image data for the surface of the sample S obtained by the CCD camera 12. Next, the CPU 61 calculates the position of the sample stage 2 when the automatic focusing has the high-magnification field lens 15A in focus and calculates the amount of offset in the vertical direction from the reference position stored in the memory 63. The CPU 61 then stores the amount of offset in the memory 63 as the correction parameter. The correction parameter is the amount of offset in the vertical direction between the position of the sample stage 2 when indentation is performed by one of the first indenter 141A and the second indenter 141B, which is disposed in the predetermined position opposite the sample S, and the position of the sample stage 2 when the high-magnification field lens 15A, which is disposed in the predetermined position, is focused. The automatic focusing and obtaining the amount of offset in the vertical direction may be performed at any time as long as the automatic focusing and obtaining the amount of offset in the vertical direction are performed after performing the process of step S16 in the process for obtaining the correction parameters and before the process for obtaining the correction parameters ends.

In the first modification example described above, the amount of offset is calculated in the order of the amount of offset in the vertical direction for the position of the sample stage 2 when the low-magnification field lens 15B is focused, then the amount of offset in the vertical direction for the position of the sample stage 2 when the high-magnification field lens 15A is focused, in order to match the order in the process for obtaining the correction parameters. However, in a case where the amount of offset in the horizontal direction is calculated in the order of the high-magnification field lens 15A, then the low-magnification field lens 15B in the process for obtaining the correction parameters, the amount of offset in the vertical direction is also calculated in the order of the high-magnification field lens 15A, then the low-magnification field lens 15B.

In addition, in step S36 of the process for hardness testing (see FIG. 16), the CPU 61 references the correction parameters stored in the memory 63 to retrieve the offset in the Z direction (i.e., the vertical direction) between the position of the sample stage 2 when indentation is performed by the second indenter 141B, which is disposed in the predetermined position before rotating the turret 16, and the position of the sample stage 2 when the low-magnification field lens 15B, which is disposed in the predetermined position after rotating the turret 16, is focused.

Next, in step S37 of the process for hardness testing, the CPU 61 raises and lowers the AF stage 4 and the elevator mechanism 5 in the vertical direction by the amount of offset in the vertical direction between the position of the sample stage 2 when indentation is performed by the second indenter 141B and the position of the sample stage 2 when the low-magnification field lens 15B is focused. Thereby, the offset in the vertical direction between the position of the sample stage 2 when indentation is performed by the second indenter 141B and the position of the sample stage 2 when the low-magnification field lens 15B is focused is corrected. Specifically, the CPU 61 is the stage displacement controller raising and lowering the AF stage 4 and the elevator mechanism 5 based on the amount of offset stored in the memory 63, such that the sample stage 2 is positioned in the position where the field lens 15 (the low-magnification field lens 15B), which is disposed in the predetermined position by the turret 16, is focused.

As described above, the hardness tester 200 according to the first modification example of the second embodiment includes the AF stage 4 and the elevator mechanism 5 raising and lowering the sample stage 2 in the vertical direction. The memory 63 stores the amount of offset in the vertical direction between the position of the sample stage 2 when indentation is performed by the indenters 141 when disposed in the predetermined position and the position of the sample stage 2 when field lenses 15 are focused when disposed in the predetermined position. The CPU 61 raises and lowers the AF stage 4 and the elevator mechanism 5 based on the amount of offset stored in the memory 63, such that the sample stage 2 is positioned in the position where the field lenses 15 are focused when disposed in the predetermined position by the turret 16. Therefore, the offset in the vertical direction due to mechanical variation arising when the indenter or field lens is swapped out, for example, can be corrected. Therefore, the burden of adjustment work on the user can be lightened.

Second Modification Example

In the hardness tester 200 according to the second embodiment, the indentations formed by the first indenter 141A and the second indenter 141B are observed by disposing the field lenses 15 in the predetermined position when the correction parameters are calculated. However, when the high-magnification field lens 15A in particular is disposed in the predetermined position to observe the indentation, the field of view is narrow as compared to the low-magnification field lens 15B. Therefore, the indentation may be impossible to locate within the obtained image. The hardness tester 200 according to a second modification example is capable of obtaining the correction parameters in a simple way even in such a case.

Figure 17:
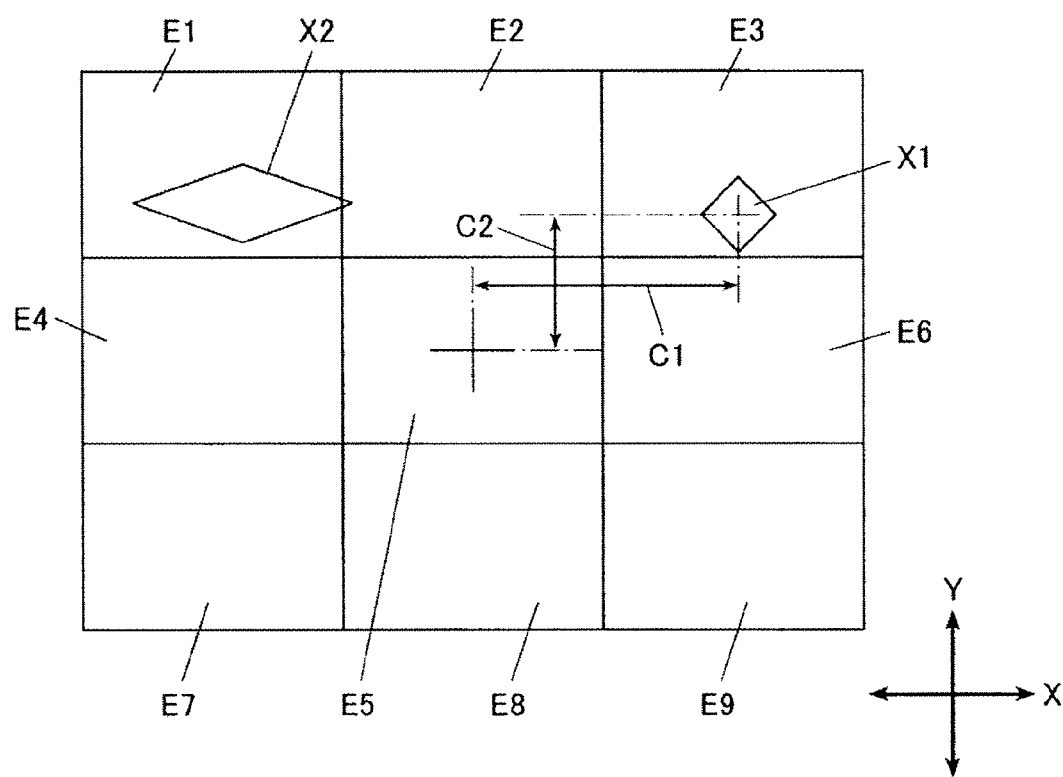
FIG. 17 illustrates an example of a compiled image in the hardness tester according to a second modification of the second embodiment.

Specifically, in the hardness tester 200 according to the second modification example, in step S17 of the process for obtaining the correction parameters (see FIG. 5), the CPU 61 analyzes the image of the surface of the sample S captured by the CCD camera 12 via the high-magnification field lens 15A (E5 in FIG. 17). The CPU 61 then determines whether the indentation formed by the first indenter 141A is present in the image E5. Specifically, the CPU 61 is an indentation determiner.

When, as a result of the above determination, the CPU 61 determines that the indentation is not present in the image E5, the CPU 61 captures a total of nine images E1 to E9 with the CCD camera 12 while displacing the XY stage 3A in the XY direction (i.e., the horizontal direction) in increments of a range enabling image capture each time an image is captured, displacement of the XY stage 3A being centered on a current position. The CPU 61 then compiles the nine captured images into a single image (see FIG. 17). Specifically, the CPU 61 is an image compiler. Moreover, a number of images to be compiled is not limited to nine. As many images as desired can be compiled.

Moreover, a specific method for compiling the images can utilize commonly known technologies or a technology presented by the applicants of the present application in Japanese Patent Laid-Open Publication No. H8-313217. Therefore, a detailed description thereof is omitted.

Next, the CPU 61 analyzes the compiled image, then calculates an amount of offset C1 in the X direction and an amount of offset C2 in the Y direction between the center position of the indentation X1, formed by the first indenter 141A, and the center position of the high-magnification field lens 15A (see FIG. 17). The CPU 61 then stores the amounts of offset C1 and C2 in the memory 63 as the correction parameters. The amount of offset in the X direction and the amount of offset in the Y direction may also be calculated between the center position of the indentation X2, formed by the second indenter 141B, and the center position of the high-magnification field lens 15A.

As described above, according to the hardness tester 200 according to the second modification example of the second embodiment, the field lenses 15 include the high-magnification field lens 15A and the low-magnification field lens 15B having a lower magnification than the high-magnification field lens 15A. The hardness tester 200 includes the indentation determiner (CPU 61) and the image compiler (CPU 61). The indentation determiner analyzes the image of the surface of the sample S captured by the CCD camera 12 via the high-magnification field lens 15A to determine whether the indentations formed by the indenters 141 are present in the image. When the indentation determiner determines that the indentations are not present in the image, the image compiler captures a desired number of images with the CCD camera 12 while displacing the XY stage 3A in the horizontal direction in increments of the range enabling image capture each time an image is captured, displacement of the XY stage 3A being centered on the current position. The image compiler then compiles the desired number of captured images into a single image. Therefore, even when the position in which the indentation is formed is outside the field of view, the correction parameters can be readily obtained. Thus, the process for obtaining the correction parameters can be performed efficiently. Moreover, the second modification example can be combined with the first modification example.

Above, a concrete description was given based on embodiments according to the present invention. However, the present invention is not limited to the above-described embodiments and may be modified within a scope not deviating from the substance of the invention.

For example, in the above-described embodiments, an exemplary configuration is described that includes two indenter axes 14 (indenters 141) and two field lenses 15. However, the present invention is not limited to this. Any number of indenter axes 14 (indenters 141) and field lenses 15 may be included so long as the configuration includes at least one indenter axis 14 (indenter 141) and at least one field lens 15. For example, the present invention may be configured to include one indenter axis 14 (indenter 141) and three field lenses 15.

In addition, within a scope not deviating from the substance of the present invention, appropriate modifications may also be made to detailed structures and operations of each component configuring the hardness testers 100 and 200.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester for measuring hardness of a sample placed on a sample stage by loading a predetermined test force on the sample with an indenter to form an indentation in a surface of the sample, then measuring dimensions of the indentation, the hardness tester comprising:
   a horizontal stage displacer configured to displace the sample stage in a horizontal direction;
   an image capturer configured to capture an image of the surface of the sample via a field lens;
   a display configured to display the image of the surface of the sample captured by the image capturer;
   a switcher configured to selectively position one of the indenter and the field lens in a predetermined position opposite the sample;
   a memory configured to store an amount of mechanical offset in the horizontal direction between a center position of the indenter when positioned in the predetermined position and a center position of the field lens when positioned in the predetermined position; and
   a display controller configured to display an indicator indicating the center position of the indenter on the display based on the amount of offset stored in the memory when the field lens is positioned in the predetermined position by the switcher.

2. The hardness tester according to claim 1, wherein:
   the indenter comprises a first indenter and a second indenter;
   the memory is configured to store the amount of offset in the horizontal direction between the center position of the first indenter when positioned in the predetermined position and the center position of the second indenter when positioned in the predetermined position; and
   the display controller is configured to display an indicator indicating the center position of the first indenter and an indicator indicating the center position of the second indenter on the display based on the amount of offset stored in the memory when the field lens is positioned in the predetermined position by the switcher.

3. The hardness tester according to claim 1, wherein the field lens is a low-magnification field lens.

4. A hardness tester for measuring hardness of a sample placed on a sample stage by loading a predetermined test force on the sample with an indenter to form an indentation in a surface of the sample, then measuring dimensions of the indentation, the hardness tester comprising:
   a horizontal stage displacer configured to displace the sample stage in a horizontal direction;
   an image capturer configured to capture an image of the surface of the sample via a field lens;
   a switcher configured to selectively position one of the indenter and the field lens in a predetermined position opposite the sample;
   a memory configured to store an amount of mechanical offset in the horizontal direction between a center position of the indenter when positioned in the predetermined position and a center position of the field lens when positioned in the predetermined position; and
   a stage displacement controller configured to displace the horizontal stage displacer to a position corresponding to a center position of one of the indenter and the field lens when positioned in the predetermined position by the switcher, based on the amount of offset stored in the memory.

5. The hardness tester according to claim 4, wherein
   the indenter includes a first indenter and a second indenter;
   the memory is configured to store the amount of offset in the horizontal direction between the center position of the first indenter when positioned in the predetermined position and the center position of the second indenter when positioned in the predetermined position; and
   the stage displacement controller is configured to displace the horizontal stage displacer to a position corresponding to the center position of one of the first indenter, the second indenter, and the field lens when positioned in the predetermined position by the switcher, based on the amount of offset stored in the memory.

6. The hardness tester according to claim 5, further comprising a stage elevator raising and lowering the sample stage in a vertical direction, wherein:
   the memory is configured to store an amount of offset in the vertical direction between a position of the sample stage when performing indentation with the indenter, the indenter being positioned in the predetermined position, and the position of the sample stage when the field lens is in focus, the field lens being positioned in the predetermined position, and
   the stage displacement controller is configured to raise and lower the stage elevator based on the amount of offset stored in the memory, such that the sample stage is positioned in the position where the field lens is in focus, the field lens being positioned in the predetermined position by the switcher.

7. The hardness tester according to claim 6, wherein the field lens comprises:
   a first field lens; and
   a second field lens having a lower magnification than the first field lens, the hardness tester further comprising:
   an indentation determiner configured to analyze the image of the surface of the sample captured by the image capturer via the first field lens and determine whether the indentation formed by the indenter is present in the image; and
   an image compiler configured to capture, when the indentation determiner determines that the indentation is not present in the image, a desired number of images with the image capturer while displacing the horizontal stage displacer in the horizontal direction in increments of a range enabling image capture each time an image is captured, displacement of the horizontal stage displacer being centered on a current position, the image compiler further to configured to then compile the desired number of captured images into a single image.

8. The hardness tester according to claim 5, wherein the field lens comprises:
   a first field lens; and
   a second field lens having a lower magnification than the first field lens, the hardness tester further comprising:
   an indentation determiner configured to analyze the image of the surface of the sample captured by the image capturer via the first field lens and determine whether the indentation formed by the indenter is present in the image; and
   an image compiler configured to capture, when the indentation determiner determines that the indentation is not present in the image, a desired number of images with the image capturer while displacing the horizontal stage displacer in the horizontal direction in increments of a range enabling image capture each time an image is captured, displacement of the horizontal stage displacer being centered on a current position, the image compiler further to configured to then compile the desired number of captured images into a single image.

9. The hardness tester according to claim 4, further comprising a stage elevator raising and lowering the sample stage in a vertical direction, wherein:
the memory is configured to store an amount of offset in the vertical direction between a position of the sample stage when performing indentation with the indenter, the indenter being positioned in the predetermined position, and the position of the sample stage when the field lens is in focus, the field lens being positioned in the predetermined position, and
the stage displacement controller is configured to raise and lower the stage elevator based on the amount of offset stored in the memory, such that the sample stage is positioned in the position where the field lens is in focus, the field lens being positioned in the predetermined position by the switcher.

10. The hardness tester according to claim 9, wherein the field lens comprises:
a first field lens; and
a second field lens having a lower magnification than the first field lens, the hardness tester further comprising:
an indentation determiner configured to analyze the image of the surface of the sample captured by the image capturer via the first field lens and determine whether the indentation formed by the indenter is present in the image; and
an image compiler configured to capture, when the indentation determiner determines that the indentation is not present in the image, a desired number of images with the image capturer while displacing the horizontal stage displacer in the horizontal direction in increments of a range enabling image capture each time an image is captured, displacement of the horizontal stage displacer being centered on a current position, the image compiler further to configured to then compile the desired number of captured images into a single image.

11. The hardness tester according to claim 4, wherein the field lens comprises:
a first field lens; and
a second field lens having a lower magnification than the first field lens, the hardness tester further comprising:
an indentation determiner configured to analyze the image of the surface of the sample captured by the image capturer via the first field lens and determine whether the indentation formed by the indenter is present in the image; and
an image compiler configured to capture, when the indentation determiner determines that the indentation is not present in the image, a desired number of images with the image capturer while displacing the horizontal stage displacer in the horizontal direction in increments of a range enabling image capture each time an image is captured, displacement of the horizontal stage displacer being centered on a current position, the image compiler further to configured to then compile the desired number of captured images into a single image.

12. The hardness tester according to claim 4, wherein the field lens is a low-magnification field lens.

* * * * *